United States Patent
Wood

(10) Patent No.: US 9,919,121 B2
(45) Date of Patent: *Mar. 20, 2018

(54) VENTILATION INTERFACE FOR SLEEP APNEA THERAPY

(71) Applicant: INNOMED TECHNOLOGIES INC., Coconut Creek, FL (US)

(72) Inventor: Thomas Wood, Waycross, GA (US)

(73) Assignee: InnoMed Healthscience, Inc., Coconut Creek, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/829,097

(22) Filed: Aug. 18, 2015

(65) Prior Publication Data

US 2015/0352312 A1 Dec. 10, 2015

Related U.S. Application Data

(63) Continuation of application No. 13/494,323, filed on Jun. 12, 2012, now Pat. No. 9,138,553, which is a (Continued)

(51) Int. Cl.
*A61M 16/06* (2006.01)
*A61M 16/20* (2006.01)
*A61M 16/08* (2006.01)

(52) U.S. Cl.
CPC ........ *A61M 16/0666* (2013.01); *A61M 16/06* (2013.01); *A61M 16/0616* (2014.02);
(Continued)

(58) Field of Classification Search
CPC ........... A62B 23/00; A62B 23/06; A62B 7/00; A62B 7/10; A62B 9/00; A61M 16/00;
(Continued)

(56) References Cited

U.S. PATENT DOCUMENTS

| 1,125,542 A | 1/1915 | Humphries |
| 3,400,714 A | 9/1968 | Sheridan |

(Continued)

FOREIGN PATENT DOCUMENTS

| GB | 0532214 | 1/1941 |
| GB | 2368533 | 5/2002 |

(Continued)

*Primary Examiner* — Rachel T Sippel
(74) *Attorney, Agent, or Firm* — Maier & Maier, PLLC

(57) ABSTRACT

The ventilation interface for sleep apnea therapy interfaces a ventilation device to the patient's airways. The ventilation interface includes a pair of nasal inserts made from flexible, resilient silicone which are oval shaped in cross-section and slightly tapered from a base proximal the ventilation supply to the distal tip end. A bead flange is disposed about the exterior of each insert at the distal end of the insert. A bleed port for release of exhaled air is defined through a conical vent projecting normally to the path of the incoming air flow, and continues through a nipple extending to the exterior of the air conduit. In one embodiment, a pair of nasal inserts are integral with a nasal cannula body, with bleed ports axially aligned with each insert. In another embodiment, each insert is independently connected to a separate, thin-walled, flexible supply line.

20 Claims, 7 Drawing Sheets

Related U.S. Application Data continuation of application No. 11/702,229, filed on Feb. 5, 2007, now abandoned, which is a continuation of application No. 10/940,989, filed on Sep. 15, 2004, now Pat. No. 7,188,624, which is a continuation-in-part of application No. 09/524,371, filed on Mar. 13, 2000, now Pat. No. 6,478,026.

(52) U.S. Cl.
CPC .... *A61M 16/0816* (2013.01); *A61M 16/0833* (2014.02); *A61M 16/20* (2013.01); *A61M 16/201* (2014.02); *A61M 16/0694* (2014.02); *A61M 2206/20* (2013.01)

(58) Field of Classification Search
CPC .......... A61M 16/0666; A61M 16/0683; A61M 16/06; A61M 2210/0618; A61M 25/02; A61F 5/08
See application file for complete search history.

(56) References Cited

U.S. PATENT DOCUMENTS

| | | |
|---|---|---|
| 3,722,509 A | 3/1973 | Nebel |
| 3,739,774 A | 6/1973 | Gregory |
| 3,754,552 A | 8/1973 | King |
| 3,861,385 A | 1/1975 | Carden |
| 3,884,223 A | 5/1975 | Keindl |
| 3,902,486 A | 9/1975 | Guichard |
| 3,905,361 A | 9/1975 | Hewson et al. |
| 4,106,505 A | 8/1978 | Salter et al. |
| 4,120,300 A | 10/1978 | Tiep |
| 4,156,426 A | 5/1979 | Gold |
| 4,267,831 A | 5/1981 | Aguilar |
| 4,267,845 A | 5/1981 | Robertson, Jr. et al. |
| 4,273,124 A | 6/1981 | Zimmerman |
| 4,278,082 A | 7/1981 | Blackmer |
| 4,312,359 A | 1/1982 | Olson |
| 4,327,719 A | 5/1982 | Childers |
| 4,367,735 A | 1/1983 | Dali |
| 4,367,816 A | 1/1983 | Wilkes |
| 4,406,283 A | 9/1983 | Bir |
| 4,422,456 A | 12/1983 | Teip |
| 4,493,614 A | 1/1985 | Chu et al. |
| 4,549,542 A | 11/1985 | Chien |
| 4,587,967 A | 5/1986 | Chu et al. |
| 4,601,465 A | 7/1986 | Roy |
| 4,617,637 A | 11/1986 | Chu et al. |
| 4,648,398 A | 3/1987 | Agdanowski et al. |
| 4,660,555 A | 4/1987 | Payton |
| 4,699,139 A | 10/1987 | Marshall et al. |
| 4,706,664 A | 11/1987 | Snook et al. |
| 4,753,233 A | 6/1988 | Grimes |
| 4,774,946 A | 10/1988 | Ackerman et al. |
| 4,899,740 A | 2/1990 | Napolitano |
| 4,915,105 A | 4/1990 | Lee |
| 4,996,983 A | 3/1991 | AmRein |
| 5,000,173 A | 3/1991 | Zalkin et al. |
| 5,022,900 A | 6/1991 | Bar-Yona et al. |
| 5,025,805 A | 6/1991 | Nutter |
| 5,038,772 A | 8/1991 | Kolbe et al. |
| 5,046,491 A | 9/1991 | Derrick |
| 5,074,297 A | 12/1991 | Venegas |
| 5,113,857 A | 5/1992 | Dickerman et al. |
| 5,121,745 A | 6/1992 | Isreal |
| 5,127,397 A | 7/1992 | Kohnke |
| 5,137,017 A | 8/1992 | Salter |
| D333,015 S | 2/1993 | Farmer et al. |
| 5,188,101 A | 2/1993 | Tumolo |
| 5,265,592 A | 11/1993 | Beaussant |
| 5,269,296 A | 12/1993 | Landis |
| 5,271,391 A | 12/1993 | Graves |
| 5,299,599 A | 5/1994 | Farmer et al. |
| 5,335,656 A | 8/1994 | Bowe et al. |
| 5,355,893 A | 10/1994 | Mick et al. |
| 5,375,593 A | 10/1994 | Press |
| 5,372,130 A | 12/1994 | Stern et al. |
| 5,385,141 A | 1/1995 | Granatiero |
| 5,394,568 A | 3/1995 | Brostrom et al. |
| 5,396,885 A | 3/1995 | Nelson |
| 5,398,673 A | 3/1995 | Lambert |
| 5,398,676 A | 3/1995 | Press et al. |
| 5,400,776 A | 3/1995 | Bartholomew |
| 5,405,339 A | 4/1995 | Kohnen |
| 5,425,359 A | 6/1995 | Liou |
| 5,437,267 A | 8/1995 | Weistein et al. |
| 5,438,981 A | 8/1995 | Starr et al. |
| 5,477,852 A | 12/1995 | Landis |
| 5,501,214 A | 3/1996 | Sabo |
| 5,509,409 A | 4/1996 | Weatherholt |
| 5,517,985 A | 5/1996 | Kirk et al. |
| 5,526,806 A | 6/1996 | Sansoni |
| 5,533,506 A | 7/1996 | Wood |
| 5,682,881 A | 11/1997 | Winthrop et al. |
| 5,740,799 A | 4/1998 | Nielson |
| 5,794,619 A | 8/1998 | Edelman et al. |
| 5,906,203 A | 5/1999 | Klockseth et al. |
| 5,954,049 A | 9/1999 | Foley et al. |
| 6,109,262 A | 8/2000 | Tovey |
| 6,192,884 B1 * | 2/2001 | Vann .................... A61M 16/00 128/204.26 |
| 6,230,708 B1 | 5/2001 | Radko |
| 6,431,172 B1 | 8/2002 | Bordewick |
| 6,478,026 B1 | 11/2002 | Wood |
| 6,561,188 B1 | 5/2003 | Ellis |
| 6,561,193 B1 | 5/2003 | Noble |
| 6,571,798 B1 | 6/2003 | Thornton |
| 6,595,215 B2 | 7/2003 | Wood |
| 6,637,434 B2 | 10/2003 | Noble |
| 6,655,385 B1 | 12/2003 | Curti et al. |
| 6,679,265 B2 | 1/2004 | Strickland et al. |
| 6,766,800 B2 | 7/2004 | Chu et al. |
| 6,776,162 B2 | 8/2004 | Wood |
| 6,807,967 B2 | 10/2004 | Wood |
| 6,863,069 B2 | 3/2005 | Wood |
| 6,938,620 B2 | 9/2005 | Payne, Jr. |
| 6,994,089 B2 | 2/2006 | Wood |
| 6,997,187 B2 | 2/2006 | Wood et al. |
| 7,059,328 B2 | 6/2006 | Wood |
| 7,188,624 B2 | 3/2007 | Wood |
| 7,234,465 B2 | 6/2007 | Wood |
| 7,472,707 B2 | 1/2009 | Wood et al. |
| RE42,843 E | 10/2011 | Strickland et al. |
| 2002/0046755 A1 | 4/2002 | DeVoss |
| 2002/0124849 A1 | 9/2002 | Billette et al. |
| 2003/0079749 A1 | 5/2003 | Strickland et al. |
| 2005/0028822 A1 | 2/2005 | Sleeper et al. |
| 2005/0033247 A1 | 2/2005 | Thompson |
| 2005/0051176 A1 | 3/2005 | Riggins |
| 2005/0061326 A1 | 3/2005 | Payne, Jr. |

FOREIGN PATENT DOCUMENTS

| | | |
|---|---|---|
| WO | 0197892 A1 | 6/2000 |
| WO | 2005/079726 A1 | 9/2005 |

\* cited by examiner

VENTILATION INTERFACE FOR SLEEP APNEA THERAPY

CROSS REFERENCE TO RELATED APPLICATIONS

This application is a continuation of U.S. patent application Ser. No. 13/494,323, filed Jun. 12, 2012, which is a continuation of U.S. patent application Ser. No. 11/702,229, filed Feb. 5, 2007, which is a continuation of U.S. patent application Ser. No. 10/940,989, filed Sep. 15, 2004, which is now U.S. Pat. No. 7,188,624, which is a continuation-in-part of U.S. patent application Ser. No. 09/524,371, filed Mar. 13, 2000, which is now U.S. Pat. No. 6,478,026, the disclosures of which are incorporated by reference herein in their entireties.

BACKGROUND OF THE INVENTION

1. Field of the Invention

The present invention relates to ventilation devices, and particularly to a ventilation device having a nasal inserts which are inserted into the nostrils and seal against the nostrils without the aid of harnesses, head straps, adhesive tape or other external devices, and having exhalation ports designed to eliminate whistling noises, the ventilation interface having particular utility in various modes of therapy for obstructive sleep apnea.

2. Description of the Related Art

Sleep apnea is a potentially lethal affliction in which breathing stops recurrently during sleep. Sleep apnea may be of the obstructive type (sometimes known as the pickwickian syndrome) in which the upper airway is blocked in spite of airflow drive; the central type with decreased respiratory drive; or a mixed type. Breathing may cease for periods long enough to cause or to exacerbate cardiac conditions, and may be accompanied by swallowing of the tongue. Sleep apnea frequently results in-fitful periods of both day and night sleeping with drowsiness and exhaustion, leaving the patient physically and mentally debilitated.

In recent years it has been found that various forms of positive airway pressure during sleep can be an effective form of therapy for the apnea sufferer. Ventilation can be applied in the form of Continuous Positive Airway Pressure (CPAP) in which a positive pressure is maintained in the airway throughout the respiratory cycle, Bilevel Positive Airway Pressure (BiPAP) in which positive pressure is maintained during inspiration but reduced during expiration, and Intermittent Mechanical Positive Pressure Ventilation in which pressure is applied when an episode of apnea is sensed. Positive airway pressure devices have traditionally employed either a face mask which only covers the patient's nose, or nasal pillows as the interface between the ventilation device and the patient's airway. However, there are problems with both of these interfaces.

The face mask requires a harness, headband, or other headgear to keep the mask in position, which many patient's find uncomfortable, particularly when sleeping. The face mask must seal the mask against the patient's face, and may cause irritation and facial sores, particularly if the patient moves his head while sleeping, causing the mask to rub against the skin. Face masks are also position dependent, and may leak if the mask changes position with movement of the patient's head. The face mask applies pressure to the sinus area of the face adjacent to the nose, causing the airways to narrow, thereby increasing the velocity of flow through the airway, but decreasing the pressure against the nasal mucosal walls. This strips moisture from the mucosal wall during inspiration, thereby causing drying and a burning sensation. These factors will often result in the patient's removal of the mask and discontinuance of positive airway pressure therapy.

Nasal pillows are pillowed style nasal seals which are pressed against the inferior portion of the nares to close the nostril openings. Nasal pillows require a headband or harness to maintain the pressure, resulting in the same patient discomfort noted with face masks. Nasal pillows have about a 0.25" internal diameter at the nasal entry port where the seal is made. Therefore, pressurized air must pass through a constricted port, increasing the velocity of airflow, with resultant drying and burning of the nasal airways. The narrowed interface diameter of the nasal pillows causes a pressure drop, which is directly proportional to the drop in the number of available air molecules within the closed system. It is the volume of air molecules at the area in the patient's throat where the apneic events appear that is needed to correct apnea. The narrower the airways or the internal diameter of the nasal interface, the lower the volume of air molecules that will be available and the greater the driving pressure that is required to meet the volume demand. An increase in driving pressure does not fully compensate for the loss in the number of air molecules available.

A further problem with existing ventilation devices is that the carbon dioxide bleed ports for venting exhaled gases are noisy on both nasal face masks and nasal pillows. The whistling noise that occurs while utilizing such devices can prove quite annoying to the patient, awakening the patient and causing the patient to discontinue use of the ventilation device.

A number of devices have been proposed which include a ventilation interface for supplying gases to be inhaled, for collecting exhaled gases, or for mounting sensors for measuring or monitoring respiratory function.

U.S. Pat. Nos. 5,335,654 and 5,535,739, issued on Aug. 9, 1994 to Rapoport and Jul. 16, 1996 is to Rapoport et al., respectively, describe a CPAP system using a conventional nasal mask, the innovation comprising a flow sensor in the input line connected to a signal processor to determine the waveform of airflow, which is connected to a flow controller to adjust the pressure of airflow as required. U.S. Des. Pat. No. 333,015, issued Feb. 2, 1993 to Farmer et al. shows an ornamental design for a nasal mask. U.S. Des. No. 262,322, issued Dec. 15, 1981 to Mizerak, shows an ornamental design for a nasal cannula with a mouth mask.

U.S. Pat. No. 4,782,832, issued Nov. 8, 1988 to Trimble et al., discloses nasal pillows held in the patient's nose by a harness arrangement, the device having a plenum with two accordion or bellows shaped nipples for fitting against the nostril openings. U.S. Pat. No. 4,774,946, issued Oct. 4, 1988 to Ackerman et al., teaches a nasal and endotracheal tube apparatus for administering CPAP to infants, the nose tubes having a bulbous portion for seating in the pares of an infant and a headband with a Velcro® closure for supporting the cannula and supply tubes.

U.S. Pat. No. 5,269,296, issued to Landis on Dec. 14, 1993, and U.S. Pat. Nos. 5,477,852 and 5,687,715, issued to Landis et al. on Dec. 26, 1995, and Nov. 18, 1997, respectively, describe CPAP devices for the treatment of sleep apnea with relatively stiff or rigid nasal cannulae or prongs surrounded by inflatable cuffs to retain the cannulae in the pares, but which also may be supplemented by an inflatable head harness to position the cannulae and hold them in place, the two cannulae being joined by a conduit having vent holes to vent exhaled air. U.S. Pat. No. 5,533,506, issued Jul. 9, 1996 to the present inventor, discloses a nasal tube: assembly in which the tubes are tapered, frustroconical assemblies with a soft membrane over the distal tip and a washer at the base of the nasal tube to prevent the tubes from falling through a support bar connected to a harness, the nasal tubes forming a positive seal with the inside of the nostrils to prevent the escape of gases.

U.S. Pat. No. 5,682,881, issued Nov. 4, 1997 to Winthrop et al., shows a nasal cannula for CPAP therapy with cone shaped nasal prongs in which the cannula is secured to the patient's upper lip by adhesive tape strips. U.S. Pat. No. 4,915,105, issued Apr. 10, 1990 to Lee, teaches a miniature respiratory breather apparatus in which relatively stiff or rigid nasal tubes have elastomeric packings for sealing the tubes in the nares.

Several patents describe improvements to nasal cannulae, but without sealing the nose tubes against the nostrils to prevent leakage of gas, including: U.S. Pat. No. 3,513,844, issued May 26, 1970 to Smith (metal strip in cannula cross-tube to retain configuration matching patient's lip); U.S. Pat. No. 4,106,505, issued Aug. 15, 1978 to Salter et al. (cannula body with ends extending upward and rearward); U.S. Pat. No. 4,915,104, issued Apr. 10, 1990 to Marcy (clasp with lanyard supporting supply tubes to ease pressure on ears); U.S. Pat. No. 5,025,805, issued Jun. 25, 1991 to Nutter (cylindrical soft sponge cuff around supply tubes to ease pressure and prevent skin injuries); U.S. Pat. No. 5,046,491, issued Sep. 10, 1991 to Derrick (device for collecting gases exhaled from both nose and mouth); U.S. Pat. No. 5,335,659, issued Aug. 9, 1994 to Pologe (device for mounting optical sensor on nasal septum); U.S. Pat. No. 5,509,409, issued Apr. 23, 1996 to Weatherholt (nasal cannula with face guards); U.S. Pat. No. 5,572,994, issued Nov. 12, 1996 to Smith (rotatable coupling in supply tubing); U.S. Pat. No. 5,636,630, issued Jun. 10, 1997 to Miller et al. (support for supply tubes); U.S. Pat. No. 5,704,916, issued Jan. 6, 1998 to Byrd (novel head strap for nasal cannula); and U.S. Pat. No. 5,704,799, issued Apr. 21, 1998 to Nielsen (device with one-way flow through cannula and flow restrictor to equalize flow into two nose members).

None of the above inventions and patents, taken either singly or in combination, is seen to describe the instant invention as claimed. Thus a ventilation interface for sleep apnea therapy solving the aforementioned problems is desired.

SUMMARY OF THE INVENTION

The ventilation interface for sleep apnea therapy interfaces a ventilation device which provides positive airway pressure (either continuous, bilevel, or intermittent) with the patient's airways. The ventilation interface includes a pair of nasal inserts made from flexible, resilient silicone which are oval shaped in cross-section and slightly tapered from a base proximal the ventilation supply to the distal tip end. A bead flange is disposed about the exterior of each insert at the distal end of the insert. A bleed port for release of exhaled air is defined through a conical vent projecting normally to the path of the incoming air flow, and continues through a nipple extending to the exterior of the air conduit. In one embodiment, a pair of nasal inserts are integral with a nasal cannula body, with bleed ports axially aligned with each insert. In another embodiment, each insert is independently connected to a separate, thin-walled, flexible supply line.

Advantageously, the construction of the nasal inserts permits the ventilation interface to be retained in the patient's nares without requiring a harness, head strap, or other-retaining device. The nasal inserts do not merely-seal the base of the nostrils, but are inserted into the nostrils farther than nasal pillows, as far as the nasal mucosal membrane, and are retained by resilient expansion of the inserts, the flanges engaging notches in the nares, together with the pressure of incoming air, which forms a positive seal to prevent the leakage of air past the inserts. The nasal inserts are constructed according to specifications which permit the inserts to be relatively thin-walled, and are oval shaped in cross-section to conform to the shape of the nostrils. This construction permits the nasal inserts to have a large internal diameter in order to pass a greater volume of air than nasal pillows or prongs, without significant narrowing of the air passages, thereby maintaining lateral pressure, and avoiding drying and burning of the patient's nasal passages, as well as supplying a sufficient number of air molecules at the desired pressure to keep the patient's airways patent. Consequently, the ventilation device is more comfortable for the patient to wear while sleeping than conventional positive airway pressure devices, but at the same time is more effective in treating the patient's apnea.

The bleed ports are specially designed to avoid the whistling noises commonly experienced with conventional nasal masks and nasal pillows. By projecting the vent structure into the air passage normal to the direction of the air flow from the supply tubes, incoming air must turn ninety degrees and exit through a long, restricted diameter bleed port to vent to the atmosphere, eliminating whistling noises to increase patient comfort. In the embodiment having a nasal cannula body, the bleed ports are axially aligned with the nasal inserts, providing $CO_2$ with a direct path to exit the cannula body. When the nasal inserts are attached to independent supply tubes, the bleed ports are at the base of the nostrils, providing essentially normal exhalation.

When the nasal inserts are directly connected to the supply tubes, the nasal inserts may be even more thin-walled than when attached to a cannula body, resulting in an even greater volume of air supplied through the cannula body, up to a 20% increase in volume. In this case the supply tubes may be similar to heat-shrink tubing, being made from a very thin-walled thermoplastic is material that is lightweight and flexible so that the supply tubing may collapse when not in use, but will expand to a predetermined diameter under pressure applied by a ventilator.

Accordingly, it is an object of the invention to provide a ventilation interface for sleep apnea therapy having nasal inserts which seal against the nares and do not require a harness, head strap, or other external devices to maintain pressure for retaining the inserts in or against the patient's nostrils.

It is another object of the invention to provide a ventilation device having nasal inserts made of flexible, resilient plastic with a bead flange for retaining the inserts in the nares, wherein the walls of the insert are thin-walled and maintain lateral pressure in the nares in order to provide a greater internal diameter for the delivery of a greater volume of air molecules at a constant delivery pressure and without forcing ventilation gases through restricted ports or passageways so that drying and burning of the patient's nasal airways is avoided while delivering a therapeutic volume of air to maintain the apneic patient's airways in a patent condition.

It is a further object ventilation interface for sleep ports to avoid whistling noises at the interface a vent passage for expired air.

Still another object of the invention is to provide a ventilation interface which is lightweight and comfortable so that the apnea patient is not tempted to discard the ventilation device is while sleeping.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
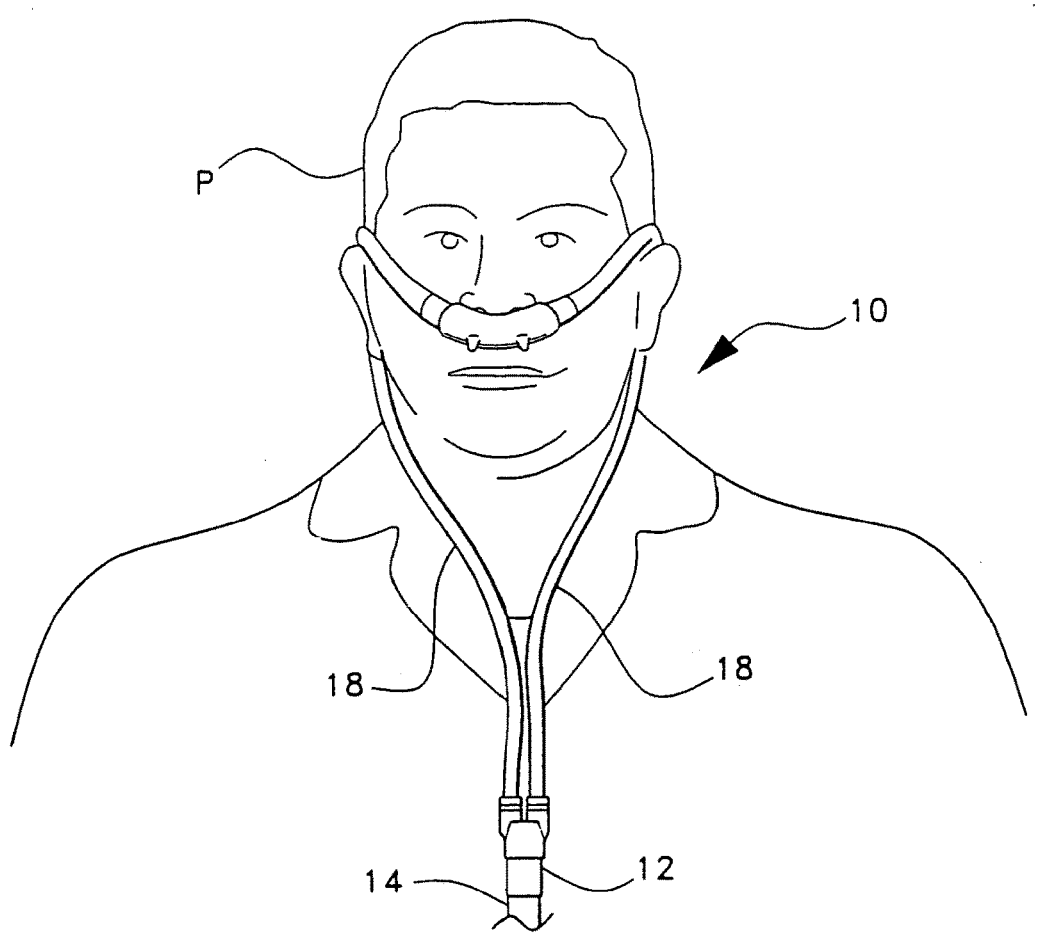
FIG. 1 is a front environmental view of a ventilation interface for sleep apnea therapy according to the present invention.
Figure 2A:
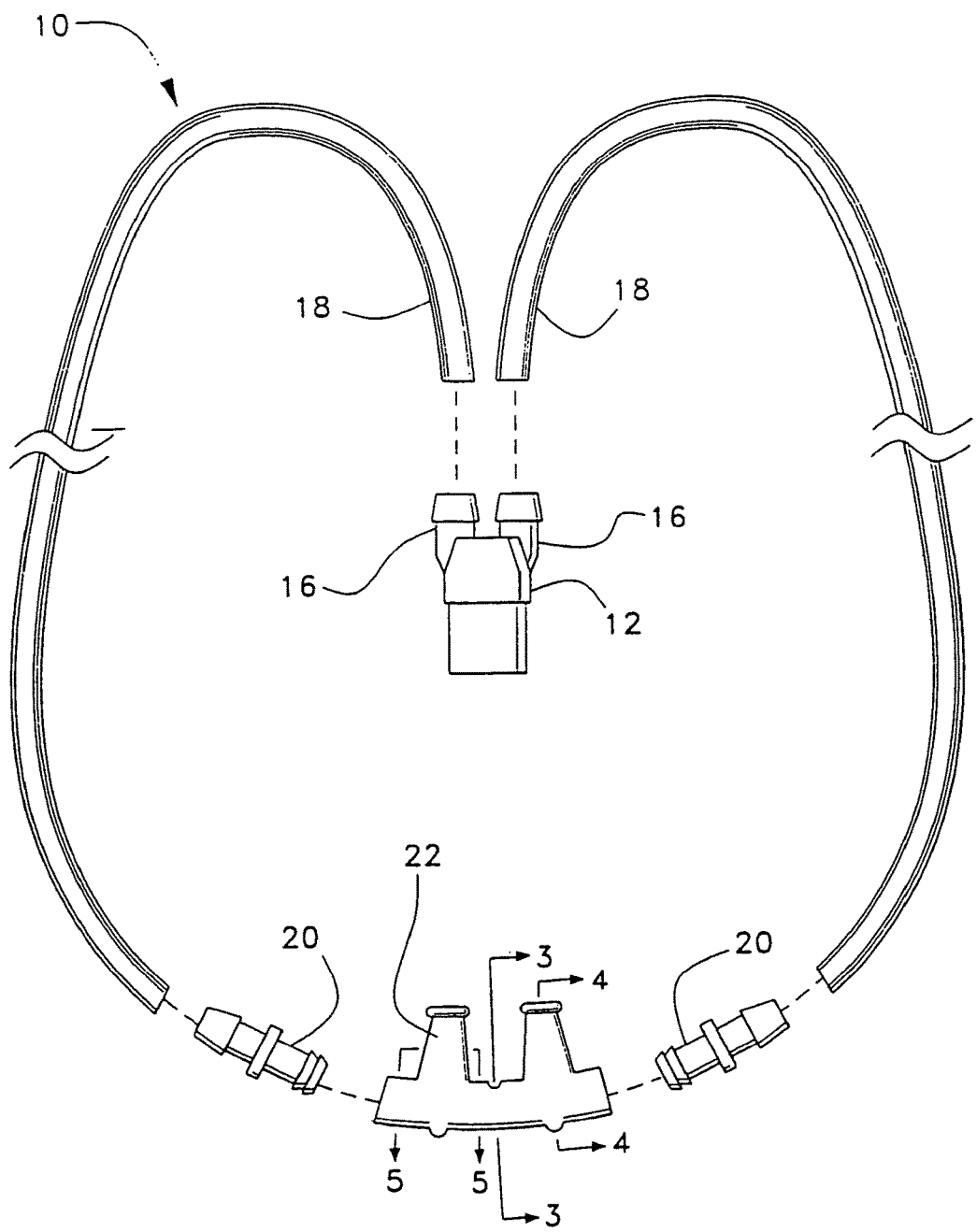
FIG. 2A is an exploded elevational of a ventilation interface according to the present invention.

The present invention is a ventilation interface for sleep apnea therapy, designated generally as 10 in the drawings. The ventilation interface 10 provides an interface for connecting a ventilation device which provides positive airway pressure (either continuous, bilevel, or intermittent) with the patient's airways. As shown in FIGS. 1 and 2A, the ventilation interface 10 includes a conventional adapter or Y-connector 12 having a first end adapted to receive a supply hose 14 from a mechanical ventilator (not shown) and a second end having a pair of ports 16 with barbed connectors for attachment to two supply tubes 18. Supply tubes 18 may be, e.g., 0.3125" ID (inside diameter) flexchem tubing, made of polyvinyl chloride or other conventional gas supply tubing. For sleep apnea therapy, the mechanical ventilator will usually supply room air at a pressure of between five and fifteen centimeters of water. The room air may be supplemented with oxygen if desired by splicing an oxygen supply line into supply hose 14 or using a triple port connector in lieu of Y-connector 12. It is normally unnecessary to humidify or add moisture to the air supplied by the mechanical ventilator in using the ventilation interface 10 of the present invention, as the interface 10 is designed to avoid stripping moisture from the nares, so that moisture does not have to be added to relieve patient discomfort from drying or burning sensation in the nasal airways.

In the embodiment shown in FIGS. 1 and 2A, the ends of the supply tubes distal from the Y-connector 12 are attached to opposite ends of a nasal cannula body 22 by barbed connectors 20. Barbed connectors 20 preferably have an inside diameter substantially equal to the inside diameter of supply tubes 18 in order to prevent any constriction or narrowing of the air passage which may cause increased velocity in air flow. Nasal cannula body 22, described more fully below, has a pair of nasal inserts 30 which are inserted into the nares of the patient P). The supply tubes may be looped over the patient's ears and joined to the Y connector 12, which may be suspended at about the patient's chest level when the patient is standing, as shown in FIG. 1. For Bi-level Positive Airway Pressure (BiPAP) or Intermittent Mechanical Positive Pressure Ventilation therapy, a suitable valve may be connected between the supply tubes 18 and the cannula body 22. An exemplary valve is described in the Applicant's prior application Ser. No. 09/524,371, filed Mar. 13, 2000, which is hereby incorporated by reference in its entirety.

Figure 2B:
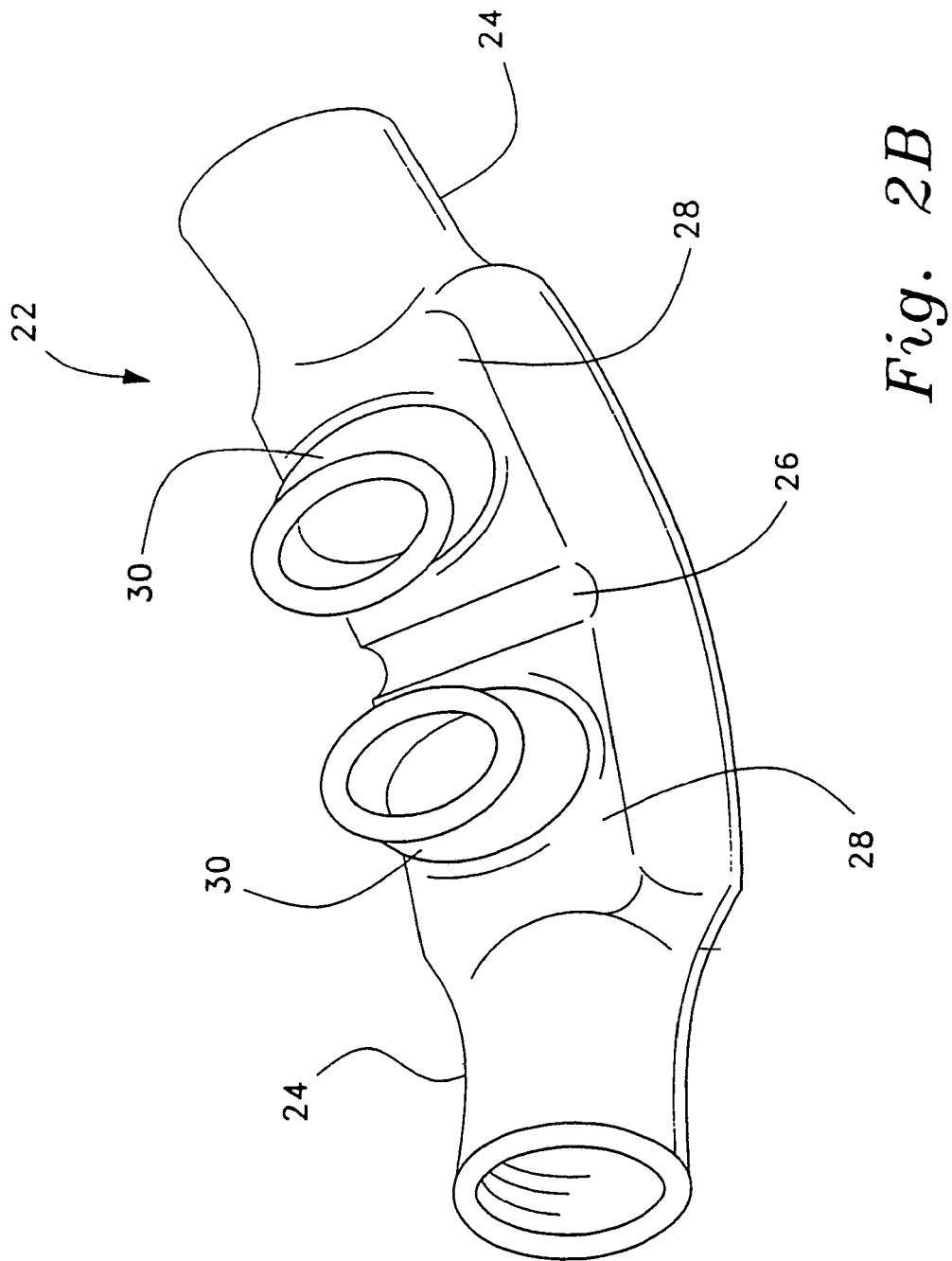
FIG. 2B is a perspective view of a ventilation interface embodied in a nasal cannula body according to the present invention.

The nasal cannula body 22 is shown in greater detail in FIG. 2B. The cannula body 22 is an arcuate, hollow, body having substantially flat top wall 22a and flat sidewalk 22b merging with a semi-cylindrical bottom wall 22c defining an air chamber 22d (seen more clearly in FIG. 3) for the passage of air and other gases, and having cylindrical tubes 24 at opposite ends which receive one end of the barbed connectors 20. A notch 26 is defined transversely across the top wall 22a of the cannula body 22, defining a pair of mounting pads 28. A pair of nasal inserts 30 are formed integral with the mounting pads 28. The nasal inserts 30 are hollow and form a continuous flow path or conduit for the passage of inhaled and exhaled gases between the patient's nasal air passages and the air chamber 22d.

Figure 3:
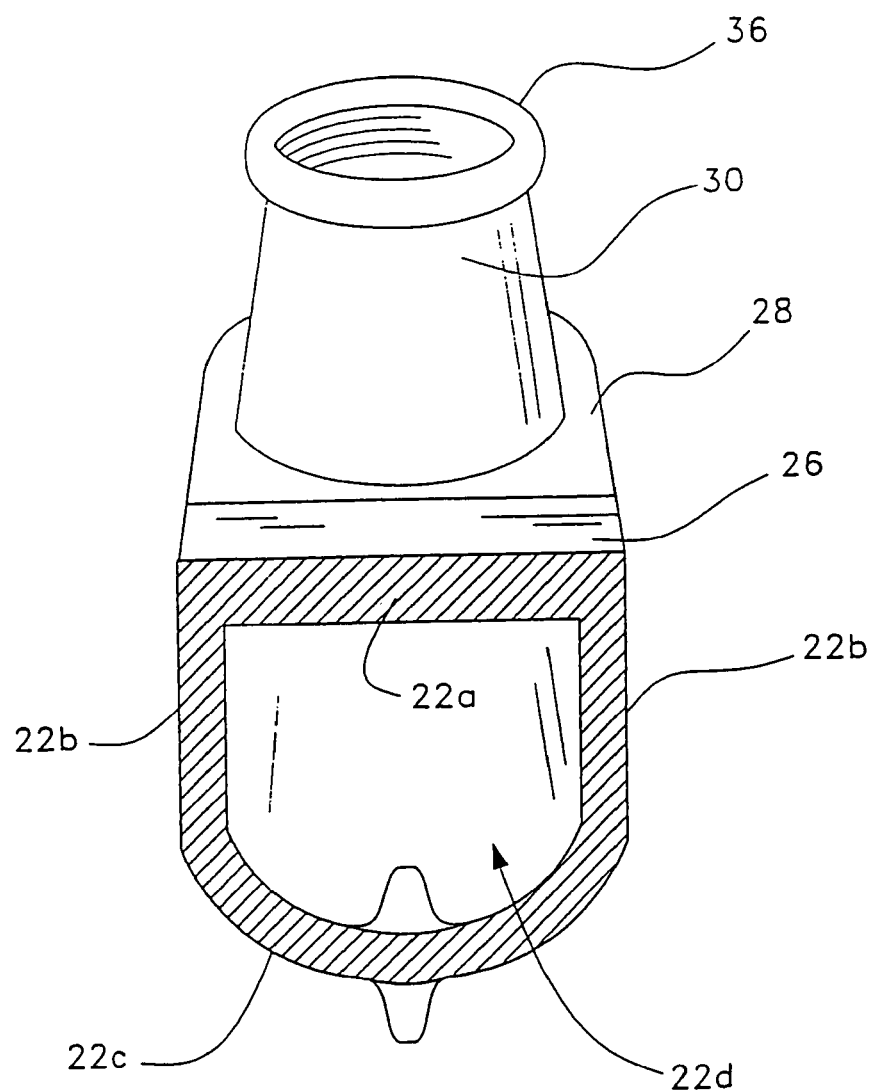
FIG. 3 is a section view along the lines 3-3 of FIG. 2A.
Figure 4:
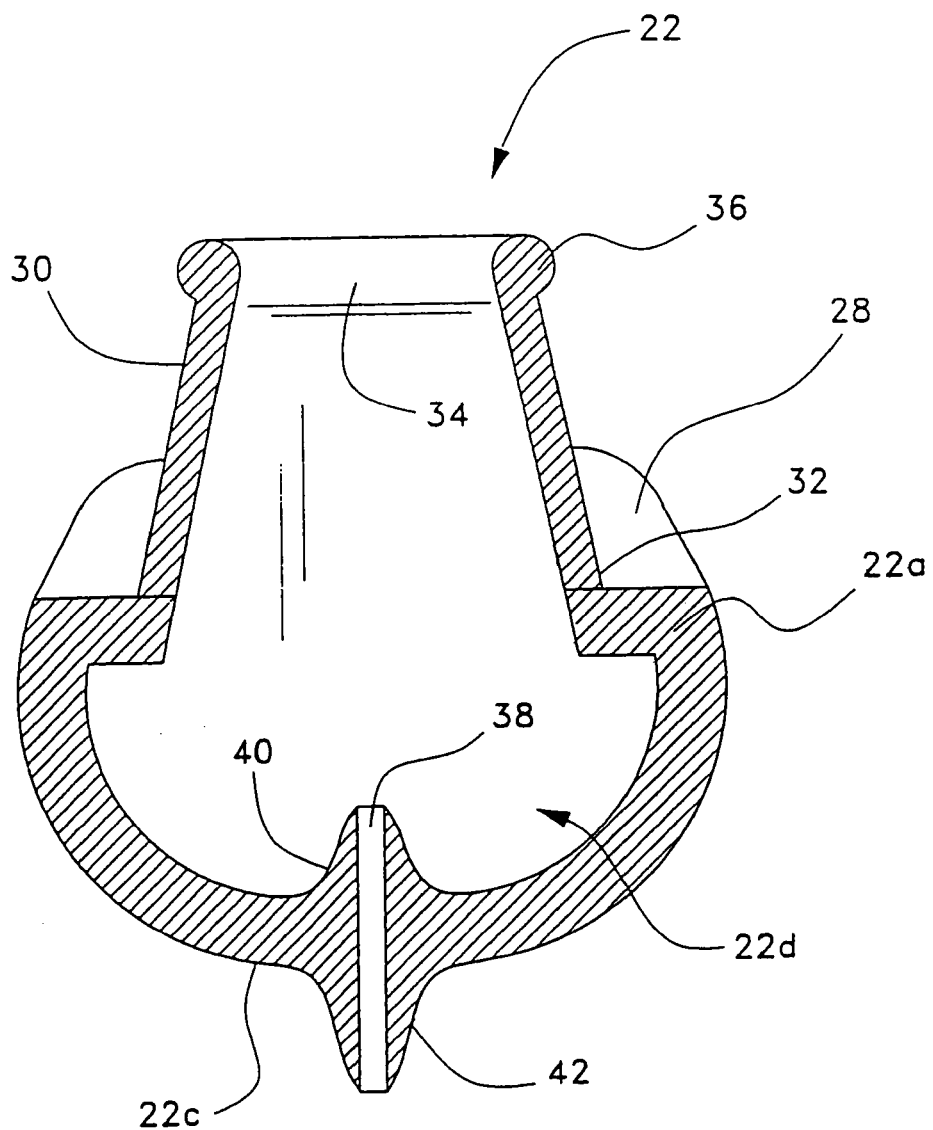
FIG. 4 is a section view along the lines 4-4 of FIG. 2A.
Figure 5:
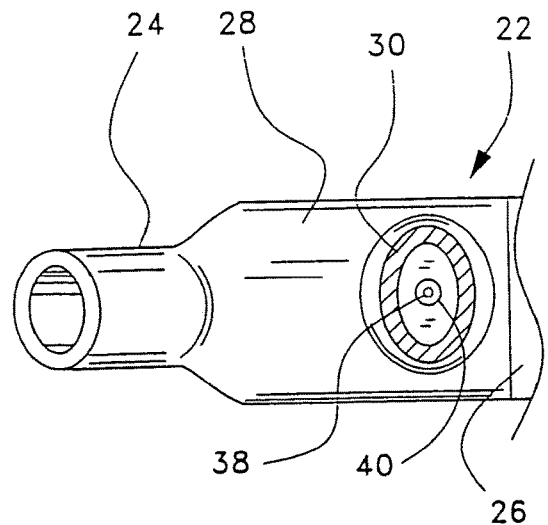
FIG. 5 is a section view along the lines 5-5 of FIG. 2A.

The nasal inserts are shown in greater detail in FIGS. 3, 4, and 5. The nasal inserts 30 are substantially oval in cross-section, with the major axis substantially parallel with the notch and the minor axis normal to the notch. The nasal inserts 30 taper slightly from a wide base 32 proximal the cannula body 22 to the open distal tip ends 34. The nasal inserts 30 have a flange 36 about the distal tip ends 34 on the exterior surface of the inserts 30, which may be formed as a semi-cylindrical bead.

The cannula body 22, including the nasal inserts 30, are preferably made from silicone elastomer. The cannula body 22 or air chamber 22d has an internal diameter of at least 0.3125 inches throughout its length. The walls of the nasal inserts 30 may be thinner than the top wall 22a. The thickness of the walls of the nasal inserts 30 are preferably between about 1/32 and 1/20 inches. The thickness of the walls at the flange 36 may be about 1/16 inches. The hardness of the walls of the nasal insert 30, as tested on a type A Shore durometer, may range between about 15 and 40, preferably about 30. If the walls of the nasal inserts 30 are made any thinner, they will fail to have sufficient integrity, and if made any thicker, they will have insufficient flexibility to form a seal against the nares. The thinness and softness of the nasal inserts 30 make them virtually unnoticeable while in the nostrils. For an adult patient, the nasal inserts may have a height of between about 0.25 and 0.75 inches. The internal diameter of the nasal inserts 30 may measure about 0.75" on the major axis and 0.5 on the minor axis, allowing for generous laminar air flow and delivering pressure more by volume of air molecules than velocity of air flow, and deliver about double the volume of nasal pillows, which have a round internal diameter of, for example, about 0.25 inches. Nasal pillows cannot be made with such large internal diameters, because it becomes difficult to create a seal under the bottom of the nose, as the pillows would have an internal diameter larger than the internal diameter of the nares, and the pillows are not as flexible as the nasal inserts 30 of the present invention.

In use, the nasal inserts 30 are inserted up the patient's nostrils until the flanges 36 lodge against the mucous membranes. As such, the nasal inserts 30 are considered an invasive device. Testing has confirmed that the nasal inserts 30 are biocompatible and meet regulatory requirements. The nasal inserts are retained in the patient's nares by the flanges 36, by the flexibility and resiliency of the silicone elastomer, and by lateral pressure of the room air, which is maintained at between five and fifteen centimeters of water. The oval cross-section of the nasal inserts 30 is shaped to conform to the normally oval shape of the nares. The relative large internal diameter of the nasal inserts 30 permits air to be supplied to the patient's airways in sufficient volume at the driving pressure without accelerating the rate of airflow that the patient has sufficient positive airway pressure to be of therapeutic value in maintaining the patient's airways patent during an episode of obstructive apnea without drying the nasal passages. The notch 26 in the top wall 22a of the cannula body 22 lends additional flexibility to the cannula body 22, so that the nasal cannula 22 can be adjusted for deviated septums, thick septums, and other anatomical variations in the configuration of the nostrils.

The cannula body 22 has a pair of bleeder ports 38 disposed in the bottom wall 22c directly below and axially aligned with the nasal inserts 30. The bleeder ports are formed by an upper conically shaped nipple 40 extending upward into the air chamber 22d, and a lower conically shaped nipple 42 extending below the bottom wall 22c. The bleeder port has an internal diameter of about three millimeters and extends for a length of about 0.25 inches. The upper nipple 40 extends about 0.125 inches into the air chamber 22d. The internal diameter of the bleeder port 38 is ample to permit venting of carbon dioxide exhaled by the patient while not being so large as to cause a significant pressure drop in the cannula body 22, and axial alignment of the bleeder port 38 with the nasal inserts 22 creates a direct path for venting of the expired gases. At the same time, laminar flow of air supplied by the supply tubes is normal to the bleeder ports 38, so that air supplied by the ventilator must bend ninety degrees to exit through the elongated bleeder port 38. The effect of this construction is that the bleeder port 38 is virtually silent in operation, eliminating the whistle associated with bleeder holes in conventional ventilation interfaces.

Figure 6:
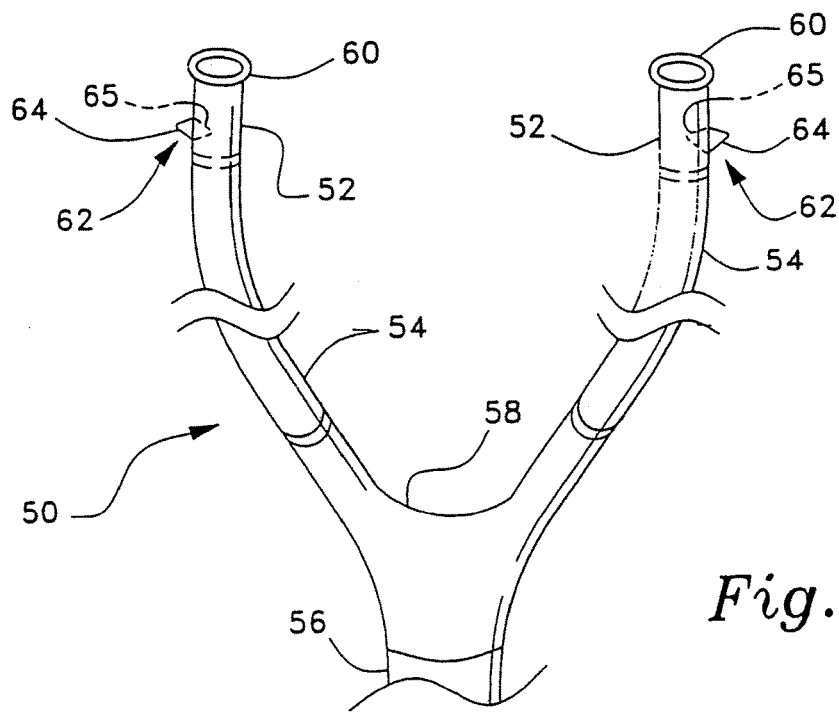
FIG. 6 is a perspective view of an embodiment of the ventilation interface with the nasal inserts incorporated into independent supply tubes.

FIG. 6 is a generally diagrammatic view of an alternative embodiment of the ventilation interface, designated 50 in the drawing. In this embodiment, each nasal insert 52 is connected to a separate supply tube 54, the supply tubes 54 being connected to the mechanical ventilator supply hose 56 by a suitable Y-connector 58 or adapter, the cannula body 22 and common air chamber 22d being omitted. The nasal inserts 52 have substantially the same construction as nasal inserts 30, being oval in cross-section and having a similar height and an annular flange 60 about the distal tip for lodging the nasal insert 52 in a naris. The nasal insert 52 is also made from silicone elastomer, and has the same softness, thickness, flexibility and resilience as the nasal insert 30. In this configuration, since the inserts are not connected to the cannula body 22, the angle at which the inserts 52 enter the nostrils is not restricted by the cannula body 22, and therefore the nares can accept a greater displacement, and may accommodate a 20% greater volume of air molecules through the insert 52 than the insert 30.

In this embodiment, the supply tubes 54 may be made from a flexible, lightweight, but relatively inelastic thermoplastic material, similar to heat shrink tubing, so that the supply tubes 54 may be at least partially collapsed in the absence of pressure from the mechanical ventilator, but expand to their maximum diameter under a pressure of between five to fifteen centimeters of water. The lightweight of the supply tubes 54 decreases any pressure on the patient's ears resulting from the weight of the supply tubes, increasing patient comfort. The bleeder ports 62 have a similar construction to the bleeder ports 38, having an internal nipple 65 normal to the axis of the nasal insert 52 and an external nipple 64, the bleeder ports 62 being just above the base of the inserts 52 and normal to the flow of supply air through the inserts 52.

It will be understood by those skilled in the art that the dimensions of the nasal inserts 30 and 52, and of the bleeder ports 38 and 62, are representative dimensions for a ventilation interface 10 or 50 designed for adults, and that the ventilation interface 10 or 50 may be made with correspondingly reduced dimensions for teenage children, preteens, and infants. It will also be understood that the nasal inserts 30 and 52 may be made from thermoplastic elastomers other than silicone, providing that the material has similar softness, resilience, flexibility, and biocompatibility. It will also be understood by those skilled in the art that the nasal inserts 30 and 52, although illustrated in conjunction with ventilation devices for the treatment of sleep apnea, may be used in any other application where it is desirable to have an interface forming a seal between at person's nasal airways and a ventilation or gas collection device, including, but not limited to, rescue breathing apparatus used by firefighters and other emergency personnel, scuba diving tanks, etc.

Figure 7:
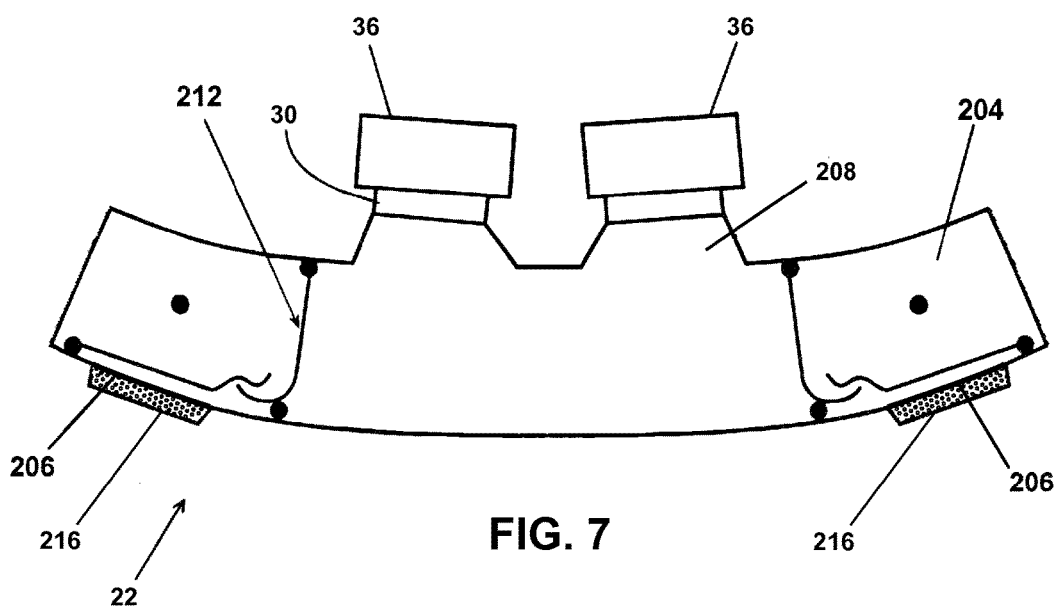
FIG. 7 is a side elevation view of an embodiment of the ventilation interface of the present invention with a valve member having a surface that has at least a portion that is exposed to unfiltered atmosphere during use.

Referring now to FIG. 7, there is provided an alternate embodiment of the present invention. Similar to the first embodiment described hereinabove, this embodiment has a hollow body 22 with at least one inhale aperture 204, at least one exhale aperture 206, and at least one and preferably two nasal apertures 208, and at least one nasal insert tube 30 removably coupled to or integrally formed with the body 22 and in fluid communication with each nasal aperture 208. At least one valve assembly 212 may be disposed within the body 22 as may be desired in a given application. One or more filters 216 may be provided in fluid communication with the exhale apertures 206.

The insert tubes 30 have annular sleeves 36 similar to those of the first embodiment such that each annular sleeve 36 forms a seal with the inner wall of the nostril and additionally exerts a force thereon sufficient to support the weight of the alternate embodiment interface in place during respiration. In this embodiment, the body 22 is not connected to interface tubing, a mechanical ventilator, or a gas supply, so the body 22 need not have tubing connectors. Instead, the interface provided is a small, lightweight, plug that is held securely in place by the annular sleeves 36.

It is to be understood that the present invention is not limited to the embodiments described above, but encompasses any and all embodiments within the scope of the following claims.

What is claimed is:

1. A valve assembly configured for coupling to a respiratory interface, the valve assembly comprising:
   at least one valve member that is configured to pivot to a closed position during exhalation;
   wherein the at least one valve member has a proximal surface and a distal surface;

wherein a majority of the distal surface of the at least one valve member is exposed to unfiltered atmosphere at the start of inspiration during use;

wherein the said respiratory interface is configured to contact at least one of the bottom of a user's nose and at least one of the user's nostrils.

2. The valve assembly of claim 1, wherein the at least one valve member repositions in response to at least one of an inhalation force and an exhalation force.

3. The valve assembly of claim 1, wherein the at least one valve member is adapted to be in at least a partially closed position during exhalation.

4. The valve assembly of claim 1, wherein the at least one valve member is configured to impede a fluid flow in at least one of a first direction and a second direction.

5. The valve assembly of claim 1, wherein the at least one valve member is configured to impede flow in a first direction more than a second direction.

6. The valve assembly of claim 1, wherein the at least one valve member is configured to impede flow in an exhalation direction more than in an inhalation direction.

7. The valve assembly of claim 1, wherein the at least one valve member is movable from a closed position during inhalation.

8. The valve assembly of claim 1, wherein the at least one valve member is adapted to be operatively associated with at least one stop.

9. The valve assembly of claim 1, wherein the at least one valve member is adapted to be operatively associated with at least one gas aperture.

10. The valve assembly of claim 1, wherein the at least one valve member is adapted to be operatively associated with at least one exhale aperture.

11. The valve assembly of claim 1, wherein the at least one valve member is adapted to at least partially close at least one exhale aperture.

12. The valve assembly of claim 1, wherein the at least one valve member is adapted to affect fluid flow through the respiratory interface.

13. The valve assembly of claim 1, wherein the at least one valve member is adapted to be operatively associated with at least one perforation.

14. The valve assembly of claim 1, wherein the at least one valve member is adapted to be operatively associated with at least one bleed port.

15. The valve assembly of claim 1, wherein the valve assembly is adapted to couple with at least one body of the respiratory interface.

16. The valve assembly of claim 1, wherein the valve assembly is adapted to couple with the respiratory interface that is adapted to be in flow communication with at least one of the user's nostrils.

17. The valve assembly of claim 1, wherein the valve assembly is adapted to couple with the respiratory interface that is adapted to contact the user's nose.

18. The valve assembly of claim 1, wherein the valve assembly is adapted to couple with the respiratory interface that is adapted to contact at least one of the user's nostrils.

19. A valve assembly configured for coupling to a respiratory interface, the valve assembly comprising:

at least one valve member that is configured to close during exhalation;

wherein the at least one valve member has a proximal surface and a distal surface;

wherein the distal surface of the at least one valve member has at least a portion that is exposed to unfiltered atmosphere at the start of inspiration during use;

wherein the said respiratory interface is adapted to traverse at least a portion of the bottom of a user's nose.

20. A valve assembly configured for coupling to a respiratory interface, the valve assembly comprising:

at least one valve member that is configured to pivot during one of inhalation and exhalation;

wherein the at least one valve member has a proximal surface and a distal surface;

wherein a majority of the distal surface of the at least one valve member is exposed to unfiltered atmosphere at the start of inspiration during use;

wherein the said respiratory interface is adapted to traverse at least a portion of the bottom of a user's nose.

* * * * *